United States Patent
Church et al.

(10) Patent No.: US 12,331,347 B2
(45) Date of Patent: Jun. 17, 2025

(54) METHODS FOR HIGH-THROUGHPUT LABELLING AND DETECTION OF BIOLOGICAL FEATURES IN SITU USING MICROSCOPY

(71) Applicant: President and Fellows of Harvard College, Cambridge, MA (US)

(72) Inventors: George M. Church, Brookline, MA (US); Je-Hyuk Lee, Allston, MA (US); Evan R. Daugharthy, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 188 days.

(21) Appl. No.: 18/157,108

(22) Filed: Jan. 20, 2023

(65) Prior Publication Data

US 2023/0227895 A1    Jul. 20, 2023

Related U.S. Application Data

(63) Continuation of application No. 16/200,831, filed on Nov. 27, 2018, now abandoned, which is a continuation of application No. 15/325,577, filed as application No. PCT/US2015/039914 on Jul. 10, 2015, now Pat. No. 10,179,932.

(60) Provisional application No. 62/023,226, filed on Jul. 11, 2014.

(51) Int. Cl.
*C12Q 1/6841* (2018.01)
*C07H 21/02* (2006.01)
*C07H 21/04* (2006.01)

(52) U.S. Cl.
CPC ........... *C12Q 1/6841* (2013.01); *C07H 21/02* (2013.01); *C07H 21/04* (2013.01)

(58) Field of Classification Search
CPC ....... C12Q 1/6841; C07H 21/02; C07H 21/04
See application file for complete search history.

(56) References Cited

U.S. PATENT DOCUMENTS

| | | | |
|---|---|---|---|
| 4,123,610 A | 10/1978 | Summerton et al. | |
| 4,844,617 A | 7/1989 | Kelderman et al. | |
| 4,886,741 A | 12/1989 | Schwartz | |
| 4,981,985 A | 1/1991 | Kaplan et al. | |
| 5,151,189 A | 9/1992 | Hu et al. | |
| 5,424,413 A | 6/1995 | Hogan et al. | |
| 5,563,056 A | 10/1996 | Swan et al. | |
| 5,594,235 A | 1/1997 | Lee | |
| 5,635,352 A | 6/1997 | Urdea et al. | |
| 5,695,940 A | 12/1997 | Drmanac et al. | |
| 5,830,708 A | 11/1998 | Naughton | |
| 5,834,758 A | 11/1998 | Trulson et al. | |
| 5,871,921 A | 2/1999 | Landegren et al. | |
| 6,068,979 A | 5/2000 | Akhavan-Tafti | |
| 6,083,726 A | 7/2000 | Mills, Jr. et al. | |
| 6,194,148 B1 | 2/2001 | Hori et al. | |
| 6,232,067 B1 | 5/2001 | Hunkapiller et al. | |
| 6,306,597 B1 | 10/2001 | Macevicz | |
| 6,534,266 B1 | 3/2003 | Singer | |
| 6,586,176 B1 | 7/2003 | Trnovsky et al. | |
| 6,632,655 B1 | 10/2003 | Mehta et al. | |
| 7,255,994 B2 | 8/2007 | Lao | |
| 7,323,305 B2 | 1/2008 | Leamon et al. | |
| 7,427,479 B2 | 9/2008 | Karger et al. | |
| 7,473,767 B2 | 1/2009 | Dimitrov | |
| 7,534,991 B2 | 5/2009 | Miller et al. | |
| 7,555,155 B2 | 6/2009 | Levenson et al. | |
| 7,655,898 B2 | 2/2010 | Miller | |
| 7,745,129 B1 | 6/2010 | Schatz | |
| 7,771,949 B2 | 8/2010 | Kramer | |
| 7,906,285 B2 | 3/2011 | Drmanac | |
| 7,910,304 B2 | 3/2011 | Drmanac | |
| 7,941,279 B2 | 5/2011 | Hwang et al. | |
| 7,989,166 B2 | 8/2011 | Koch et al. | |
| 8,013,134 B2 | 9/2011 | Fredriksson | |
| 8,124,751 B2 | 2/2012 | Pierce et al. | |
| 8,199,999 B2 | 6/2012 | Hoyt et al. | |
| 8,268,554 B2 | 9/2012 | Schallmeiner | |
| 8,329,404 B2 | 12/2012 | McKeman et al. | |
| 8,330,087 B2 | 12/2012 | Domenicali | |
| 8,415,102 B2 | 4/2013 | Geiss et al. | |
| 8,431,691 B2 | 4/2013 | McKernan et al. | |
| 8,460,865 B2 | 6/2013 | Chee et al. | |
| 8,462,981 B2 | 6/2013 | Determan et al. | |
| 8,501,459 B2 | 8/2013 | Chen et al. | |
| 8,519,115 B2 | 8/2013 | Webster et al. | |
| 8,551,710 B2 | 10/2013 | Bernitz et al. | |
| 8,658,361 B2 | 2/2014 | Wu et al. | |
| 8,697,359 B1 | 4/2014 | Zhang | |
| 8,871,445 B2 | 10/2014 | Cong et al. | |
| 8,906,616 B2 | 12/2014 | Zhang et al. | |
| 8,932,814 B2 | 1/2015 | Cong et al. | |
| 8,946,389 B2 | 2/2015 | Gao et al. | |
| 8,986,926 B2 | 3/2015 | Ferree et al. | |
| 8,993,233 B2 | 3/2015 | Zhang et al. | |
| 8,999,641 B2 | 4/2015 | Zhang et al. | |
| 9,017,992 B2 | 4/2015 | Winther et al. | |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Stougaard (2007, BMC Biotechnology, 2007, 7:69, pp. 1-10).*

(Continued)

*Primary Examiner* — Sarae L Bausch
(74) *Attorney, Agent, or Firm* — Banner & Witcoff, Ltd.

(57) ABSTRACT

Methods of labelling one or more subcellular components (e.g., an organelle and/or subcellular region) in vivo are provided. Methods of labelling a protein in vivo are provided. Methods of determining a nucleic acid sequence in situ are also provided.

14 Claims, 6 Drawing Sheets
Specification includes a Sequence Listing.

(56) References Cited

U.S. PATENT DOCUMENTS

| | | |
|---|---|---|
| 9,201,063 B2 | 12/2015 | Sood et al. |
| 9,217,151 B2 | 12/2015 | Yin et al. |
| 9,257,135 B2 | 2/2016 | Ong et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 10,030,261 B2 | 7/2018 | Frisen et al. |
| 10,032,064 B2 | 7/2018 | Hoyt |
| 10,126,242 B2 | 11/2018 | Miller et al. |
| 10,138,509 B2 | 11/2018 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,872,679 B2 | 12/2020 | Cai et al. |
| 10,964,001 B2 | 3/2021 | Miller |
| 11,021,737 B2 | 6/2021 | Church et al. |
| 11,078,520 B2 | 8/2021 | Church et al. |
| 11,111,521 B2 | 9/2021 | Church et al. |
| 11,118,220 B2 | 9/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,566,277 B2 | 1/2023 | Church et al. |
| 11,639,518 B2 | 5/2023 | Church et al. |
| 2002/0015952 A1 | 2/2002 | Anderson et al. |
| 2002/0029979 A1 | 3/2002 | Freund et al. |
| 2002/0155989 A1 | 10/2002 | Efimov et al. |
| 2002/0172950 A1 | 11/2002 | Kenny et al. |
| 2003/0148335 A1 | 8/2003 | Shen et al. |
| 2003/0165852 A1 | 9/2003 | Schueler et al. |
| 2004/0077014 A1 | 4/2004 | Becker |
| 2004/0081979 A1 | 4/2004 | Knezevic et al. |
| 2004/0248144 A1 | 12/2004 | Mir |
| 2004/0259190 A1 | 12/2004 | Naughton |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0190543 A1 | 8/2007 | Livak |
| 2007/0206275 A1 | 9/2007 | Hemmer et al. |
| 2007/0231823 A1 | 10/2007 | McKernan et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0180790 A1 | 7/2008 | Tafas et al. |
| 2008/0269068 A1 | 10/2008 | Church et al. |
| 2009/0005259 A1 | 1/2009 | Drmanac |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0280559 A1 | 11/2009 | McCarthy |
| 2010/0009868 A1 | 1/2010 | Yan et al. |
| 2010/0047924 A1 | 2/2010 | Webster et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0288249 A1 | 10/2013 | Gullberg et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0004598 A1 | 1/2015 | Gao et al. |
| 2015/0005188 A1 | 1/2015 | Levner et al. |
| 2015/0098126 A1 | 4/2015 | Keller et al. |

(56) References Cited

U.S. PATENT DOCUMENTS

| | | |
|---|---|---|
| 2015/0133319 A1 | 5/2015 | Fu et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0024555 A1 | 1/2016 | Church et al. |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0376642 A1 | 12/2016 | Landegren et al. |
| 2017/0009278 A1 | 1/2017 | Soderberg et al. |
| 2017/0067096 A1 | 3/2017 | Wassie et al. |
| 2017/0081489 A1 | 3/2017 | Rodriques et al. |
| 2017/0010672 A1 | 4/2017 | Luo et al. |
| 2017/0176338 A1 | 6/2017 | Wu et al. |
| 2017/0191078 A1 | 7/2017 | Zhang et al. |
| 2017/0212983 A1 | 7/2017 | Cai et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0051322 A1 | 2/2018 | Church et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1 | 10/2018 | Walter et al. |
| 2019/0017106 A1 | 1/2019 | Frisen et al. |
| 2019/0032128 A1 | 1/2019 | Chen et al. |
| 2019/0119735 A1 | 4/2019 | Deisseroth et al. |
| 2019/0203275 A1 | 7/2019 | Frisen et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0115504 A1 | 4/2021 | Cai et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| CN | 1580283 A | 2/2005 |
| CN | 1959384 A | 5/2007 |
| CN | 101553306 A | 10/2009 |
| EP | 2878671 A1 | 6/2015 |
| JP | H04-268359 A | 9/1992 |
| JP | 2007-526772 A | 9/2007 |
| JP | 2009-538123 A | 11/2009 |
| JP | 2012-170337 A | 9/2012 |
| JP | 2014-513523 A | 6/2014 |
| JP | 2015-090458 A | 5/2015 |
| KR | 20080003402 A | 1/2008 |
| WO | 9746704 A1 | 12/1997 |
| WO | 98/56955 A1 | 12/1998 |
| WO | 0126708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008/108989 A2 | 9/2008 |
| WO | 2008157696 A2 | 12/2008 |
| WO | 2009/046348 A1 | 4/2009 |
| WO | 2009046149 A1 | 4/2009 |
| WO | 2010/054108 A2 | 5/2010 |
| WO | 2010080134 A1 | 7/2010 |
| WO | 2010/087325 A1 | 8/2010 |
| WO | 2010104533 A2 | 9/2010 |
| WO | 2011/143124 A2 | 11/2011 |
| WO | 2011143583 A1 | 11/2011 |
| WO | 2012005595 A2 | 1/2012 |
| WO | 2012058638 A2 | 5/2012 |
| WO | 2012/110899 A2 | 8/2012 |
| WO | 2012150035 A1 | 11/2012 |
| WO | 2012/164565 A1 | 12/2012 |
| WO | 2013055995 A2 | 4/2013 |
| WO | 2013096851 A1 | 6/2013 |
| WO | 2013/098244 A1 | 7/2013 |
| WO | 2013/126794 A1 | 8/2013 |
| WO | 2013119827 A1 | 8/2013 |
| WO | 2013/141680 A1 | 9/2013 |
| WO | 2013/142578 A1 | 9/2013 |
| WO | 2013176772 A1 | 11/2013 |
| WO | 2014/022702 A2 | 2/2014 |
| WO | 2014/048083 A1 | 4/2014 |
| WO | 2014/065596 A1 | 5/2014 |
| WO | 2014/089290 A1 | 6/2014 |
| WO | 2014/093595 A1 | 6/2014 |
| WO | 2014/093622 A2 | 6/2014 |
| WO | 2014/093661 A2 | 6/2014 |
| WO | 2014/093694 A1 | 6/2014 |
| WO | 2014099744 A1 | 6/2014 |
| WO | 2014/113493 A1 | 7/2014 |
| WO | 2014/144288 A1 | 9/2014 |
| WO | 2014/150624 A1 | 9/2014 |
| WO | 20140163886 A1 | 10/2014 |
| WO | 2014182528 A2 | 11/2014 |
| WO | 2014/191518 A1 | 12/2014 |
| WO | 2014/197568 A2 | 12/2014 |
| WO | 2015/127183 A2 | 8/2015 |
| WO | 2015118029 A1 | 8/2015 |
| WO | 2016007839 A1 | 1/2016 |
| WO | 2016081740 A1 | 5/2016 |
| WO | 2017079382 A1 | 5/2017 |
| WO | 2017079406 A1 | 5/2017 |
| WO | 2017143155 A2 | 8/2017 |
| WO | 2017/161251 A1 | 9/2017 |
| WO | 2017189525 A1 | 11/2017 |

OTHER PUBLICATIONS

Mali, P. et al. RNA-Guided Human Genome Engineering Via Cas9. Science. Jan. 3, 2013, vol. 339; pp. 823-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.

Tiley, LS et al. The VP16 Transcription Activation Domain Is Functional When Targeted To A Promoter-Proximal RNA Sequence. Genes and Development. 1992. vol. 6; pp. 2077-2087; abstract; p. 2077, first column, first paragraph.

Trafton, A. Editing The Genome With High Precision [online]. MIT News office. Jan. 3, 2013 [retrieved on Dec. 4, 2014). Retrieved from the Internet: <URL:http:/Inewsoffice. Trafton .edut20 13/editing-the-genome-with-high-precision-01 03 >;pp. 1-3; p. 3, third paragraph.

Leman, AR et al. The Replication Forie Understanding The Eukaryotic Replication Machinery And The Challenges To Genome Duplication. Genes. Jan. 29, 2013. vol. 4; pp. 1-32; figure 1; DOI: 10.3390/genes4010001.

(56) References Cited

OTHER PUBLICATIONS

Qi, L et al. Repurposing CRISPR As An RNA-Guided Platform For Sequence-Specific Control Of Gene Expression. Cell. Feb. 28, 2013. vol. 152; pp. 1173-1183; figures 2, 4. DOI: 10.1 016/j.cell.2013.02.022.

Gasiunas, G et aL Cas9-crRNA Ribonucleoprotein Complex Mediates Specific DNA Cleavage For Adaptive Immunity In Bacteria. PNAS. Sep. 4, 2012. vol. 109, No. 39; pp. E2579-E2586; p. E2583, first column, first paragraph. DOI: 1 0.1073/pnas.1208507109.

Cong, Let al. Multiplex Genome Engineering Using CRISPR/Cas Systems. Science. Jan. 3, 2013, vol. 339; pp. 819-823; abstract; p. 821, third column; p. 822, first column, first paragraph; figure 4. DOI: 10.1126/science.1231143.

Jinek, M et al. A Programmable Dual-RNA-Guided DNA Endonuclease In Adaptive Bacterial Immunity. Science. Jun. 28, 2012. vol. 337; pp. 816-821; DOI: 10.1126/science.1225829.

CRISPR In The Lab: A Practical Guide [online]. Addgene. Sep. 4, 2014. Retrieved on Dec. 4, 2014. Retrieved from the Internet: <URL: https://www.addgene.org/CRISPR/guide/>.

Cheng, AW et al. Multiplexed Activation Of Endogenous Genes By CRISP R-on, An RNA-Guided Transcriptional Activator System. Cell Research. Aug. 27, 2013. vol. 23; pp. 1163-1171. DOI: 10.1038/cr.2013.122.

Mali, P. et al. CAS9 Transcriptional Activators For Target Specificity Screening And Paired Nickases For Cooperative Genome Engineering. Nature Biotechnology. Aug. 1, 2013. vol.31; pp. 833-838; entire document. DOI: 10.1038/nbt.2675.

Ran, FA et al. Double Nicking By RNA-Guided CRISPR Cas9 For Enhanced Genome Editing Specificity. Cell. Sep. 12, 2013. vol. 154; pp. 1380-1389. DOI: 10.1016/j.cell.2013.08.021.

International Search Report and Written Opinion issued in corresponding International Application No. PCT/US14/40868, mailed Dec. 31, 2014.

Al-Attar et al., Clustered Regularly Interspaced Short Palindromic Repeats (CRISPRs): The Hallmark of an Ingenious Antiviral Defense Mechanism in Prokaryotes, Bioi Chern. (20 11) vol. 392, Issue 4, pp. 277-289.

Carroll, "A CRSIPR Approach to Gene Targeting" 20(9) Molecular Therapy 1658-1660 (Sep. 2012).

Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. entire document.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Makarova et al., "Evolution and classification of the CRISPR-Cas systems" 9(6) Nature Reviews Microbiology 467-477 (1-23) (Jun. 2011).

Rho, Mina et al. 'Diverse CRISPRs Evolving in Human Microbiomes.' PLoS Genetics. vol. 8, No. 6. 1-14 pp. 1-12. Jun. 2012. entire document.

Sontheimer Erik, Project 7: Establishing RNA-Directed DNA Targeting in Eukaryotic Cells; Project dates: Nov. 16, 2011 to Dec. 31, 2012 (Feb. 4, 2012).

Wiedenheft et al., "RNA-guided genetic silencing systems in bacteria and archaea" 482 Nature 331-338 (Feb. 16, 2012).

Dec. 18, 2014 (PCT) International Preliminary Report—App PCT/US2013/044241.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

Thisse et al. "High-Resolution in situ hybridization to whole-mount zebrafish embryos" 2008. Nature Protocols. vol.3 No. 1 pp. 59-69. Doi:10.1038/nprot.2007.514.

Extended European Seach Report issued in corresponding European Application No. 12860433.7, dated Aug. 13, 2015.

International Search Report and Written Opinion issued in corresponding International Application No. PCT/US2012/071398, mailed Apr. 8, 2013.

Benner et al. "Gene Expression analysis by massively parallel signature sequencing (MPSS) on microbead arrays". Nature Biotechnology, vol. 18, pp. 630-634 (Jun. 31, 2000).

Han et al. "Quantum-dot-tagged microbeads for multiplexed optical coding of biomolecules". Nature Biotechnology, vol. 19, 99. 631-635 (Jul. 31, 2001).

Office Action issued for corresponding European Patent Application No. 12780609.9, dated Sep. 23, 2015.

Liu et al, Cell-Penetrating Peptide-Mediated Delivery of TALEN Proteins via Bioconjugation for Genome Engineering, PLOS One, 2014, vol. 9(1), pp. 1-7.

Ramakrishna et al, Gene disruption by cell-penetrating peptide-mediated delivery of Cas9 protein and guide RNA, Genome Res. published online Apr. 2, 2014, pp. 1-20 plus figures.

The Delivery Problem, Nature Biotechnology, 2006, vol. 24(3), pp. 305-306.

Ansari et al, Rioactivators: Transcription activation by non-coding RNA, Grit Rev Biochem Mol Bioi. 2009 ; 44(1 ): 50-61.

Sapranauskas et al (Nucleic Acids Research, 2011, 39:9275-9282).

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Ascano, M et al. Identification Of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Ginart, P et al. RNA Sequencing In Situ. Nat Biotechnol. Jun. 2014, vol. 32, No. 6; pp. 543-544; DOI: 10.1038/nbt.2921.

Saliba, AE et al. Single-Cell RNA-Seq: Advances And Future Challenges. Nucleic Acids Res. Jul. 22, 2014, vol. 42, No. 14; pp. 8845-8860; DOI: 10.1093/nar/gku555.

U.S. Appl. No. 61/794,422, filed Mar. 15, 2013, Davis, G. et al.

U.S. Appl. No. 61/781,598, filed Mar. 14, 2013, Haurwitz, R.

Gilbert, Luke A., et al.,"CRISPR-Mediated Modular RNA-Guided Regulation of Transcription in Eukaryotes," Cell, vol. 154, No. 2, Jul. 1, 2013 (Jul. 1, 2013), pp. 442-451.

Mali, P. et al., "Supplementary Materials for RNA-Guided Human Genome Engineering via Cas9," Science, vol. 339, No. 6121, Jan. 3, 2013 (Jan. 3, 2013), pp. 1-36.

Maeder, Morgan L., et al.,"Robust, synergistic regulation of human gene expression using TALE activators," HHS Public Access Author Manuscript, vol. 10, No. 3, Feb. 10, 2013 (Feb. 10, 2013), pp. 243-245.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

Eliscovich et al. mRNA on the move: The road to its biological destiny. Journal of Biological Chemistry, vol. 288, No. 28, pp. 20361-20368, Jul. 2013, in press May 2013 (Year: 2013).

Weis et al. Protein targeting to subcellular organelles via mRNA localization. Biochimica et Biophysica Acta, vol. 1833, pp. 260-273, 2013, available online Apr. 2012 (Year: 2012).

Jambhekar et al. Cis-acting determinants of asymmetric, cytoplasmic RNA transport. RNA, vol. 13, pp. 625-642, 2007 (Year: 2007).

Singer-Kruger et al. Here, there, everywhere. RNA Biology, vol. 11, No. 8, pp. 1031-1039, Aug. 2014. (Year: 2014).

Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).

Chen, et al. "Spatially resolved, highly multiplexed RNA profiling in single cells". Science. Apr. 24, 2015;348(6233):aaa6090, pp. 1-14.

(56) References Cited

OTHER PUBLICATIONS

Tam, et al. A microfluidic platform for correlative live-cell and super-resolution microscopy. PloS one. Dec. 29, 2014;9(12):e115512, pp. 1-20.
Bálint, et al. Correlative live-cell and superresolution microscopy reveals cargo transport dynamics at microtubule intersections. Proceedings of the National Academy of Sciences. Feb. 26, 2013;110(9): pp. 3375-3380.
Manders, et al. Direct imaging of DNA in living cells reveals the dynamics of chromosome formation. The Journal of cell biology. Mar. 8, 1999;144(5):813-822.
Nakano et al. "Effects of Molecular Crowding on the Structures, Interactions, and Functions of Nucleic Acids" Chemical Reviews; 2014; 114; pp. 2733-2758.
Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).
Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year: 2009).
Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).
Grompe (1993) Nature Genetics DOI: 10.1038/ng1093-111.
Seo, et al. Four-color DNA sequencing by synthesis on a chip using photocleavable fluorescent nucleotides. Proceeding of the National Academy of Sciences, Apr. 2005, 102 (17) 5926-5931.
Brenner, et al. "Gene expression analysis by massively parallel signature sequencing (MPSS) on microbead arrays". Nature Biotechnology vol. 18, pp. 630-634 (2000) doi: 10.1038/76469.
Thisse et al. 2008 Nature protocols vol. 3 No. 1 pp. 59-69. Doi:10.1038/nprot.2007.514.
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
International Search Report and Written Opinion based on PCT/US2018/027583 issued Jun. 29, 2018.
Soderberg, Ola et al., "Direct observation of individual endogenous protein complexes in situ by proximity ligation," Nature Methods, Dec. 2006, pp. 995-1000, vol. 3, No. 12, Nature Publishing Group.
Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.
Cao, Yi et al.," In-situ immuno-PCR to detect antigens," The Lancet, Sep. 16, 2000, pp. 1002-1003, vol. 356.
Sano, Takeshi et al. "Immuno-PCR: Very Sensitive Antigen Detection by Means of Specific Antibody-DNA Conjugates," Science, Oct. 2, 1992, pp. 120-122, vol. 258.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].
Extended European Search Report issued May 13, 2019 for EP Application No. 16862929.3.
Lee, Je Hyuk et al., "Fluorescent in situ sequencing (FISSEQ) or RNA for gene expression profiling in intact cells and issues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Extended European Search Report issued May 21, 2019 for European Application No. 16862945.9.
Choi, Harry M.T. et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.
Extended European Search Report issued for EP Application No. 17790240.0 on Sep. 4, 2019.
Brown et al., Review Article : In situ Hybridization with Riboprobes : An Overview for Veterinary Pathologists. Veterinary Pathology 35 : 159-167 (Year: 1998).
Choi et al.,Programmable in situ amplification for multiplexed imaging of mRNA expression. Nature Biotechnology 28(11): 1208 (Year: 2010).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Hansen et al., Sensitive ligand-based protein quantification using immuno-PCR: A critical review of single-probe and proximity ligation assays. Biotechniques 56:217-228 (Year: 2014).
Kuimelis et al., Cleavage properties of an oligonucleotide containing a bridged internucleotide 5-phosphorothioate RNA linkage. Nucleic Acids Research 23 (23) : 4753-4760 (Year: 1999).
Mag et al., Synthesis and selective cleavage of an oligodeoxynucleotide containing a bridged internucleotide 5'- phosphorothioate linkage. Nucleic Acids Research 19(7): 1437 (Year: 1991).
Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year: 2012).
Srinivas et al., On the biophysics and kinetics of toehold-mediated DNA strand displacement. Nucleic Acids Research 41 (22) : 10641-10658 (Year: 2013).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Weibrecht, Irene et al., "Simultaneous Visualization of Both Signaling Cascade Activity and End-Point Gene Expression in Single Cells", PLOS One, vol. 6, No. 5, May 25, 2011 (May 25, 2011).
Larsson, Chatarina; Grundberg, Ida; Sbderberg, Ola; Nilsson, Mats: ll In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] * the whole document *.
Nuovo: "Co-labeling Using In Situ PCR: A Review "Journal of Histochemistry & CYTOCHEMISTRY, vol. 49, No. 11, Nov. 1, 2001 (Nov. 1, 2001), pp. 1329-1339, XP055164942, ISSN: 0022-1554, DOI: 10.1177/002215540104901101 * the whole document *.
Mitra R. D. et al: ll In situ localized amplification and contact replication of many individual DNA molecules ll Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 * abstract *.
Ke et al: ll In situ sequencing for RNA analysis in preserved tissue and cells ll Nature Methods, vol. 10, No. 9, Jul. 14, 2013 (Jul. 14,

(56) References Cited

OTHER PUBLICATIONS

2013), pp. 857-860, XP055163946, ISSN: 1548-7091, DOI: 10.1038/nmeth.2563 * the whole document *.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.
Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Nadji et al.,"Photochemically and Photoenzymatically Cleavable DNA," J. Am. Chem. Soc. 1992, 114, 9266-9269.
Extended European Search Report and Written Opinion issued Dec. 17, 2019 for EP 19180827.8.
Supplementary European Search Report and Written Opinion issued Mar. 18, 2020.
Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Chen et al., "Nanoscale imaging of RNA with expansion microscopy," Nature Methods, vol. 133, No. 8, pp. 679-684 (Aug. 1, 2016).
Preliminary Office Action issued by Brazilian Patent Office on Apr. 7, 2020.
Supplementary European Search Report issued Apr. 9, 2020 for EP 17847555.
Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).
Terry R, Porreca G, McCarthy K, Church GM. 2008. Polonator Instrument https://web.archive.org/ web/20080905133800/http://www.polonator.org; Wayback Machine (Sep. 5, 2008) "Polony Sequence by Ligation Protocol".
Terry R, Porreca G, McCarthy K, Church GM. 2008. Polonator Instrument https://web.archive.org/web/20080705172604/http://www.polonator.org; Wayback Machine (Jul. 5, 2008) "Polony Sequence Protocols".
Terry R, Porreca G, McCarthy K, Church GM. 2008. Polonator Instrument https://web.archive.org/web/20080905133818/http://www.polonator.org; Wayback Machine (Sep. 5, 2008) "Help Wanted".
Terry R, Porreca G, McCarthy K, Church GM. 2008. Polonator Instrument https://web.archive.org/web/20080807155529/http://www.polonator.org/software.aspx; Wayback Machine (Aug. 7, 2008) "Software".
Terry R, Porreca G, McCarthy K, Church GM. 2008. Polonator Instrument https://web.archive.org/web/20080807155404/http://www.polonator.org; Wayback Machine (Aug. 7, 2008) "Reagent Kits".
Terry R, Porreca G, McCarthy K, Church GM. 2008. Polonator Instrument https://web.archive.org/web/20080905133541/http://www.polonator.org/reagentkits/run.aspx; Wayback Machine (Sep. 5, 2008) "Run Kits".
Terry R, Porreca G, McCarthy K, Church GM. 2008. Polonator Instrument https://web.archive.org/web/20080905133601/http://www.polonator.org/reagentkits.pairedtag.aspx; Wayback Machine (Sep. 5, 2008) "Paired-Leg Library Kits".
Terry R, Porreca G, McCarthy K, Church GM. 2008. Polonator Instrument https://web.archive.org/web/20080905133741/http://www.polonator.org/reagentkits.emulsion.aspx; Wayback Machine (Sep. 5, 2008) "Emulsion PCR/Bead Capping Kits".
Terry R, Porreca G, McCarthy K, Church GM. 2008. Polonator Instrument https://web.archive.org/web/20080905133702/http://www.polonator.org/reagentkits/enrichment.aspx; Wayback Machine (Sep. 5, 2008) "Enrichment Kits".
Terry R, Porreca G, McCarthy K, Church GM. 2008. Polonator Instrument https://web.archive.org/web/20080807155316/http://www.polonator.org/flowcells.aspx; Wayback Machine (Aug. 7, 2008) "Flow Cells".
Church GM. 2006. "Genomes for all" Sci Am 294: 46-54.
De Bakker PI, Yelensky R, Pe'er I, Gabriel SB, Daly MJ, Altshuler D. 2005. "Efficiency and power in genetic association studies" Nat Genet 37: 1217-23.
Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39:1202-7.
Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.
Risch N, Merikangas K. 1996. "The future of genetic studies of complex human diseases" Science 273: 1516-7.
Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422: 297-302.
Altshuler D, Daly MJ, Lander ES. 2008. "Genetic mapping in human disease" Science 322: 881-8.
Cookson W, Liang L, Abecasis G, Moffatt M, Lathrop M. 2009. "Mapping complex disease traits with global gene expression" Nat Rev Genet 10: 184-94.
International HapMap C. 2005. "A haplotype map of the human genome" Nature 437: 1299-320. PMC ID: PMC1880871.
Klein RJ. 2007. "Power analysis for genome-wide association studies" BMC Genet 8: 58. PMC ID: PMC2042984.
Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.
McCarroll SA. 2008. "Extending genome-wide association studies to copy-number variation" Hum Mol Genet 17:R135-42.
Morley M, Molony CM, Weber TM, Devlin JL, Ewens KG, Spielman RS, Cheung VG. 2004. "Genetic analysis of genome-wide variation in human gene expression" Nature 430: 743-7.
Sachidanandam et al., Nature, 2001, vol. 409, pp. 928-933.
Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.
Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.
Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.
Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.
Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.

(56) References Cited

OTHER PUBLICATIONS

Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hafler D, Daly MJ, Altshuler D. 2008. "Genetic analysis of human traits in vitro: drug response and gene expression in lymphoblastoid cell lines" PLoS Genet 4: e1000287. PMC ID: PMC2583954.
Christian AT, Pattee MS, Attix CM, Reed BE, Sorensen KJ, Tucker JD. 2001. "Detection of DNA point mutations and mRNA expression levels by rolling circle amplification in individual cells" Proc Natl Acad Sci U S A 98: 14238-43. PMC ID: PMC64666.
Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).
Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.
Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.
Kolb HC, Finn Mg, B. SK. 2001. "Click Chemistry: Diverse Chemical Function from a Few Good Reactions" Angew. Chem. Int. 40: 2004-21.
Kwiatkowski M, Fredriksson S, Isaksson A, Nilsson M, Landegren U. 1999. "Inversion of in situ synthesized pligonucleotides: improved reagents for hybridization and primer extension in DNA microarrays" Nucleic Acids Res 27: 4710-4. PMC ID: PMC148770.
Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.
Mitra RD, Butty VL, Shendure J, Williams BR, Housman DE, Church GM. 2003. "Digital genotyping and haplotyping with polymerase colonies" Proc Natl Acad Sci U S A 100: 5926-31. PMC ID: PMC156303.
Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.
Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC ID: PMC2203993.
Wang Z, Gerstein M, Snyder M. 2009. "RNA-Seq: a revolutionary tool for transcriptomics" Nat Rev Genet 10: 57-63.
Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.
Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).
Bakal C, Aach J, Church G, Perrimon N. 2007. "Quantitative morphological signatures define local signaling networks regulating cell morphology" Science 316: 1753-6.
Bang D, Church GM. 2008. "Gene synthesis by circular assembly amplification" Nat Methods 5: 37-9.
Bell J. 2004. "Predicting disease using genomics" Nature 429: 453-6.
Eid et al. Science, 2009, vol. 323, pp. 133-138.
Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.
Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.
Kurimoto K, Yabuta Y, Ohinata Y, Saitou M. 2007. "Global single-cell cDNA amplification to provide a template for representative high-density oligonucleotide microarray analysis" Nat Protoc 2: 739-52.
Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular acticaion of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.
Zhou et al. "In Situ Detection of Messenger RNA Using Digoxigenin-Labeled Oligonucleotides and Rolling Circle Amplification" Experimental and Molecular Pathology 70, 281-288 (2001).
May 29, 2020—Examination Report issued for EP 18173059.9.
Official Notification issued May 24, 2020 for IL 242959.
Jun. 1, 2020—Examination Report issued for GB 1809029.0.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Jun. 2, 2020—(JP) Notice of Reasons for Rejection for App. No. 2019-039027.
Supplemental Material for Schweitzer et al. (PNAS 2000; 97(18):10113-10119) (Year: 2000).
Aug. 3, 2020—(US) Non-Final Office Action—U.S. Appl. No. 16/157,243.
Aug. 3, 2020 (US) Non-Final Office Action—U.S. Appl. No. 16/393,215.
Jul. 2, 2020—(US) Non-Final Office Action—U.S. Appl. No. 16/255,920.
Aug. 10, 2020—(GB) Examination Report—GB App. No. 1809029.0.
Jul. 3, 2020—(AU) Examination Report for App. No. 20202039777.
Aug. 19, 2020—(MX) Office Action—App. No. MX/a/2015/016798.
Sep. 10, 2020—(CA) Office Action—App. No. 2,914,638.
Sep. 24, 2020—(US) Final Office Action—U.S. Appl. No. 15/772,652.
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
Sep. 25, 2020—(US) Non-Final Office Action—U.S. Appl. No. 16/386,337.
Aug. 25, 2020—(JP) Notice of Reasons for Rejection—App. No. 2018-522985.
PI: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.
Sep. 14, 2020—(CA) Examination Report—App. No. 2,850,509.
Sep. 21, 2020—(NZ) First Examination Report—App. No. 715280.
Sep. 21, 2020—(NZ) First Examination Report—App. No. 753950.
Fu et al., "Improving CRISPR-Cas nuclease specificity using truncated guide RNAs," Nature Biotechnology, vol. 32, pp. 249-284 (Jan. 26, 2014).

(56) References Cited

OTHER PUBLICATIONS

Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).
Sep. 21, 2020—(NZ) First Examination Report—App. No. 753951.
Sep. 25, 2020—(RU) Office Action—App. No. 2019114706.
DiCarlo et al., "Genome engineering in *Saccharomyces cerevisiae* using CRISPR-Cas systems," Nucleic Acids Research, vol. 41, No. 7, pp. 4336-4343 (2013).
Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.
Nov. 10, 2020—(US) Non-Final Office Action—U.S. Appl. No. 16/285,292.
Pihlak et al. "Rapid genome sequencing with short universal tiling probes" Nature Biotechnology, vol. 26, No. 6, Jun. 2008, pp. 676-684.
Lizardi "Next-generation sequencing-by-hybridization" Nature Biotechnology, vol. 26, No. 6, Jun. 2008, pp. 649-650.
Mignardi et al. "Fourth-generation sequencing in the cell and the clinic" Genome Medicine, 2014, 6:31.
Dec. 24, 2020 (US)—Notice of Allowance—U.S. Appl. No. 16/393,215.
Terry R, Porreca G, McCarthy K, Church GM. 2008. Polonator Instrument https://web.archive.org/web/20080807155459/http://www.polonator.org/index.htm; Wayback Machine (Aug. 7, 2008) "Open, Affordable, Sequencing . . . ".
Terry R, Porreca G, McCarthy K, Church GM. 2008. Polonator Instrument https://web.archive.org/web/20080807155600/http://www.polonator.org;/vision.aspx; Wayback Machine (Aug. 7, 2008) "The Vision".
Terry R, Porreca G, McCarthy K, Church GM. 2008. Polonator Instrument https://web.archive.org/web/20080807155250/http://www.polonator.org/ecosystem; Wayback Machine (Aug. 7, 2008) "The Polonator Ecosystem".
Terry R, Porreca G, McCarthy K, Church GM. 2008. Polonator Instrument https://web.archive.org/web/20080807155759/http://www.polonator.org/instrument; Wayback Machine (Aug. 7, 2008) "Instrument Overview".
Terry R, Porreca G, McCarthy K, Church GM. 2008. Polonator Instrument https://web.archive.org/web/20080807155857/http://www.polonator.org; Wayback Machine (Aug. 7, 2008) "Protocols".
Terry R, Porreca G, McCarthy K, Church GM. 2008. Polonator Instrument https://web.archive.org/web/2008090513362/http://www.polonator.org/protocols/pet.aspx; Wayback Machine (Sep. 5, 2008) "PET (Paired End-Tag) Genomic Shotgun Library Construction Protocol".
Terry R, Porreca G, McCarthy K, Church GM. 2008. Polonator Instrument https://web.archive.org/web/20080905133855/http://www.polonator.org/protocols/pcr.aspx; Wayback Machine (Sep. 5, 2008) "Emulsion PCR Protocol".
Terry R, Porreca G, McCarthy K, Church GM. 2008. Polonator Instrument https://web.archive.org/web/20080905133913/http://www.polonator.org; Wayback Machine (Sep. 5, 2008) "Emulsion Breaking Protocol".
Terry R, Porreca G, McCarthy K, Church GM. 2008. Polonator Instrument https://web.archive.org/web/20080905133837/http://www.polonator.org/protocols/beadenrichment.aspx; Wayback Machine (Sep. 5, 2008) "Bead Enrichment Protocol".
Terry R, Porreca G, McCarthy K, Church GM. 2008. Polonator Instrument https://web.archive.org/web/20080905133372/http://www.polonator.org/protocols.beadcapping.aspx; Wayback Machine (Sep. 5, 2008) "Bead Capping Protocol".
Terry R, Porreca G, McCarthy K, Church GM. 2008. Polonator Instrument https://web.archive.org/web/20080905133372/http://www.polonator.org/protocols/coverslip.aspx; Wayback Machine (Sep. 5, 2008) "Coverslip Aminosilanation and Arraying Protocol".
Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.
Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.
Mitra RD, Shendure J, Olejnik J, Edyta Krzymanska O, Church GM. 2003. "Fluorescent in situ sequencing on polymerase colonies" Anal Biochem 320: 55-65.
Porreca GJ, Shendure J, Church GM. 2006. "Polony DNA sequencing" Curr Protoc Mol Biol Chapter 7: Unit 7 8.
Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.
Shendure J, Mitra RD, Varma C, Church GM. 2004. "Advanced sequencing technologies: methods and goals" Nat Rev Genet 5: 335-44.
Shendure JA, Porreca GJ, Church GM. 2008. "Overview of DNA sequencing strategies" Curr Protoc Mol Biol Chapter 7: Unit 7 1.
Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.
Vigneault F, Sismour AM, Church GM. 2008." Efficient microRNA capture and bar-coding via enzymatic oligonucleotide adenylation" Nat Methods 5: 777-9.
Zhang K, Martiny AC, Reppas NB, Barry KW, Malek J, Chisholm SW, Church GM. 2006. "Sequencing genomes from single cells by polymerase cloning" Nat Biotechnol 24: 680-6.
Zhang K, Zhu J, Shendure J, Porreca GJ, Aach JD, Mitra RD, Church GM. 2006. "Long-range polony haplotyping of individual human chromosome molecules" Nat Genet 38: 382-7.
Church et al.; Center for Casual Consequences of Variation (CCV) "An NHGRI Center for Excellence in Genomic Science" https://web.archive.org/web/20110703211120/http://ccv.med.harvard.edu/; Wayback Machine (Jul. 3, 2011).
Church et al.; Center for Casual Consequences of Variation (CCV) "Our four Specific Aims" https://web.archive.org/web/20110813071548//http://ccv.med.harvard.edu/specific_aims.htm; Wayback Machine (Aug. 13, 2011).
Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).
J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.
May 17, 2021 (US) Notice of Allowance—U.S. Appl. No. 17/122,168.
Jun. 18, 2021 (US) Non-Final Office Action—U.S. Appl. No. 15/772,652.
May 8, 2021—(CN) Office Action—App. No. 201680077501.7.
Jul. 2, 2021—(US) Non-Final Office Action—U.S. Appl. No. 17/238,642.
Jul. 21, 2021 (US) Non-Final Office Action—U.S. Appl. No. 16/693,611.
Ho et al. "Sequencing by ligation variation with endonuclease V digestion and deoxyinosine-containing query oligonucleotides" BMC Genomics, 2011, 12:598.
Jiang et al. "Solar thermal polymerase chain reaction for smartphone-assisted molecular diagnostics" Scientific Reports, 4:4137, 2014.
Ju et al. "Four-color DNA sequencing by synthesis using cleavable fluorescent nucleotide reversible terminators" PNAS, Dec. 26, 2006, vol. 103, No. 52, pp. 19635-19640.
Lubeck et al. "Single cell in situ RNA profiling by sequential hybridization" Nature Methods, Apr. 2014, 11(4), pp. 360-361.

(56) References Cited

OTHER PUBLICATIONS

Parinov et al. "DNA sequencing by hybridization to microchip octa- and decanucleotides extended by stacked pentanucleotides" Nucleic Acids Research, 1996, vol. 24, No. 15, pp. 2998-3004.
Schouten et al. "Relative quantification of 40 nucleic acid sequences by multiplex ligation-dependent probe amplification" Nucleic Acids Research, 2002, vol. 30, No. 12, e57.
Jul. 23, 2021 (US) Non-Final Office Action—U.S. Appl. No. 16/170,751.
Aug. 16, 2021—(US) Non-Final Office Action—U.S. Appl. No. 17/363,097.
Guo et al. "Target-driven DNA association to initiate cyclic assembly of hairpins for biosensing and logic gate operation" Chemical Science, 2015, 6, pp. 4318-4323.
Aug. 10, 2021—(GB) Examination Report—App. No. 1904335.5.
Tillberg et al., "Protein-retention expansion microscopy of cells and tissues labeled using standard fluorescent proteins and antibodies," Nat Biotechnol., vol. 34, No. 9, pp. 987-992 (2016).
Chen et al., "Nanoscale imaging of RNA with expansion microscopy," Nature Methods, vol. 13, No. 8, pp. 679-684 (Aug. 1, 2016).
Jul. 6, 2021—(JP) Notice of Reasons for Rejection—App. No. 2019-511929.
Oct. 5, 2021—(EP) Summons to Oral Proceedings—App. No. 17790240.0.
Wang et al. "Rapid and Sensitive Detection of Severe Acute Respiratory Syndrome Coronavirus by Rolling Circle Amplification" Journal of Clinical Microbiology, vol. 43, No. 5, May 2005, pp. 2339-2344.
Nov. 1, 2021—(US) Final Office Action—U.S. Appl. No. 16/830,372.
Oct. 5, 2021—(JP) Notice of Reasons for Rejection—App. No. 2019-511921.
Goransson et al. "A single molecule array for digital targeted molecular analyses" Nucleic Acids Research, 2009, vol. 37, No. 1, e7, doi:10.1093/nar/gkn921.
Dirks et al. "Triggered amplificaiton by hybridization chain reaction" PNAS; Oct. 26, 2004; vol. 101, No. 43, pp. 15275-15278.
Lubeck et al. "Single cell systems biology by super-resolution imaging and combinatorial labeling" Nature Methods; 9(7); pp. 743-748; 2012.
Nov. 23, 2021 (US)—Non-Final Office Action—U.S. Appl. No. 17/392,325.
Nov. 30, 2021—(US) Final Office Action—U.S. Appl. No. 15/772,652.
Chen et al. "Functional organization of the human 4D Nucleome" PNAS, vol. 112, No. 26, Jun. 15, 2015, pp. 8002-8007.
Jarvius et al. "Digital quantification using amplified single-molecule detection" Nature Methods, vol. 3, No. 9, Sep. 2006, pp. 725-727.
Jan. 25, 2022—(US) Non-Final Office Action—U.S. Appl. No. 17/266,151.
Dec. 16, 2021—(CN) Office Action—App. No. 201780039335.6.
Jan. 28, 2022—(US) Non-Final Office Action—U.S. Appl. No. 17/366,127.
Dirks et al. "Triggered amplification by hybridization chain reaction" PNAS; Oct. 26, 2004; vol. 101, No. 43, pp. 15275-15278.
Feb. 18, 2022 (US)—Final Office Action—U.S. Appl. No. 16/170,751.
Mar. 4, 2022—(US) Non-Final Office Action—U.S. Appl. No. 17/395,534.
Feb. 8, 2022—(JP) Notice of Reasons for Rejection—App. No. 2021-028931.
Mar. 22, 2022—(US) Final Office Action—U.S. Appl. No. 17/392,325.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Capodieci et al. "Gene expression profiling in single cells within tissue" Nature Methods, Sep. 14, 2005, 2(9) pp. 663-665.
Conze et al. "Single molecule analysis of combinatorial splicing" Nucleic Acids Research, Jun. 29, 2010, vol. 38, No. 16; e163.
Femino et al. "Visualization of Single RNA Transcripts in Situ" Science, Apr. 24, 1998, vol. 280, pp. 585-590.
Gavrilovic et al. "Automated Classification of Multicolored Rolling Circle Products in Dual-Channel Wide-Field Fluroescence Microscopy" Cytometry Part A, Jul. 2011, 79(7), pp. 518-527.
Geiss et al. "Direct multiplexed measurement of gene expression with color-coded probe pairs" Nature Biotechnology, vol. 26, No. 3, Mar. 2008, pp. 317-325.
Gunderson et al. "Decoding Randomly Ordered DNA Arrays" Genome Research, May 2004, 14(5), pp. 870-7.
Han et al. "Quantum-dot-tagged microbeads for multiplexed optical coding of biomolecules" Nature Biotechnology, Jul. 2001, vol. 19, No. 7, pp. 631-5.
Tzkovitz et al. "Validating Transcripts with Probes and Imaging Technology" Nature Methods, Apr. 2011, 8(4 Suppl): S12-S19.
Itzkovitz et al. "Single molecule transcript counting of stem cell markers in the mouse intestine" Nat Cell Biol., Nov. 2011, 14(1), pp. 106-114.
Lagunavicius et al. "Novel application of Phi29 DNA polymerase: RNA detection and analysis in vitro and in situ by target RNA-primed RCA" RNA, May 2009, 15(5), pp. 765-771.
Larsson et al. "In situ detection and genotyping of individual mRNA molecules" Nature Methods, vol. 7, No. 5, May 2010, pp. 395-7.
Levsky et al. "Fluorescence in situ hybridization: past, present and future" Journal of Cell Science, Jul. 15, 2003, 116(Pt 14), pp. 2833-8.
Levsky et al. "Single-Cell Gene Expression Profiling" Science, Aug. 2, 2002, 297(5582), pp. 836-840.
Maierhofer et al. "Multicolor Deconvolution Microscopy of Thick Biological Specimens" American Journal of Pathology, vol. 162, No. 2, Feb. 2003, pp. 373-9.
Meade et al. "Multiplexed DNA detection using spectrally encoded porous" Analytical Chemistry, Apr. 1, 2009, 81(7), pp. 2618-2625.
Meade et al. "Multiplexed DNA detection using spectrally encoded porous SiO2 phtonic crystal particles" Analytical Chemistry, Apr. 1, 2009, 81(7), pp. 2618-2625.
Raj et al. "Imaging individual mRNA molecules using multiple singly labeled probes" Nature Methods, Oct. 2009, 5(10), pp. 877-879.
Sun et al. "Composite Organic-Inorganic Nanoparticles as Raman Labels for Tissue Analysis" Nano Letters, Feb. 2007, vol. 7, No. 2, pp. 351-356.
Wahlby et al. "Sequential Immunofluorescence Staining and Image Analysis for Detection of Large Numbers of Antigens in Individual Cell Nuclei" Cytometry, Jan. 1, 2002, 47(1), pp. 32-41.
Weibrecht et al. "Simultaneous Visualization of Both Signaling Cascade Activity and End-Point Gene Expression in Single Cells" PLoS One, May 2011, vol. 6, Issue 5, e20148.
Wilson et al. "Encoded Microcarriers For High-Throughput Multiplexed Detection" Angewandte Chemie International Edition, Sep. 18, 2006, 45(37), pp. 6104-17.
Zhao et al. "Advances of multiplex and high throughput biomolecular detection technologies based on encoding microparticles" Science China Chemistry, Aug. 2011, vol. 54, No. 8, pp. 1185-1201.
Jun. 14, 2022—(US) Non-Final Office Action—U.S. Appl. No. 17/584,959.
Jun. 1, 2022—(EP) Examination Report—App. No. 16862929.3.
Ng et al., "Surface-based mapping of gene expression and probabilistic expression maps in the mouse cortex," Methods, vol. 50, No. 1, pp. 55-62 (Feb. 1, 2010).
Jun. 29, 2022—(US) Non-Final Office Action—U.S. Appl. No. 17/671,803.
Jul. 5, 2022—(JP) Notice of Reasons for Rejection—App. No. 2019-511921.
Leuchowius et al. "Parallel visualization of multiple protein complexes in individual cells in tumor tissue" Molecular & Cellular Proteomics; vol. 12; No. 6; pp. 1563-1571; Jun. 2013; published online Feb. 22, 2013.
Marblestone et al. "Rosetta Brains: A strategy for molecularly-annotated connectomics" arXiv:1404.5103v1 -q-bio.NC], https://doi.org/10.48550/arXiv.1404.5103, pp. 1-18; Apr. 21, 2014.
Jul. 21, 2022—(US) Non-Final Office Action—U.S. Appl. No. 16/200,831.
Aug. 25, 2022—(EP) Examination Report—App. No. 17847555.4.

(56) References Cited

OTHER PUBLICATIONS

Douse et al. "Multiplexed and Reiterative Fluorescence Labeling via DNA Circuitry" Bioconjug Chem. Dec. 15, 2010;21(12):2327-31. doi: 10.1021/bc100348q. Epub Nov. 16, 2010.
Douse et al. "Multiplexed and Reiterative Fluorescence Labeling via DNA Circuitry" Bioconjug Chem. Dec. 15, 2010;21(12):2327-31. doi: 10.1021/bc100348q. Epub Nov. 16, 2010. (Supporting Information).
Choi et al. "Programmable in situ amplification for multiplexed bioimaging" Nature Biotechnology 28: 1208-1212, Oct. 2010, Supplementary Information.
Sep. 15, 2022—(US) Non-Final Office Action—U.S. Appl. No. 16/170,751.
Muller et al. "Towards unlimited colors for fluorescence in-situ hybridization (FISH)" Chromosome Research; 10: 223-232, 2002.
Dec. 5, 2022—(US) Non-Final Office Action—U.S. Appl. No. 17/392,325.
Drmanac et al. "Human Genome Sequencing Using Unchained Base Reads on Self-Assembling DNA Nanoarrays" Science; vol. 327; pp. 78-81; Jan. 1, 2010.
Islam et al. "Characterization of the single-cell transcriptional landscape by highly multiplex RNA-seq" Genome Research; vol. 21; May 4, 2011; pp. 1160-1167.
Larsson et al. "In situ detection and genotyping of individual mRNA molecules" Nature Methods; vol. 7; No. 5; May 2010; pp. 395-397.
Larsson et al. "In situ genotyping individual DNA molecules by target-primed rolling-circle amplification of padlock probes" Nature Methods; vol. 1; No. 3; Dec. 2004; pp. 227-232.
Shendure et al. "Accurate Multiplex Polony Sequence of an Evolved Bacterial Genome" Science; vol. 309; Sep. 9, 2005; pp. 1728-1732.
Christian et al. "Detection of DNA point mutations and mRNA expression levels by rolling circle amplification in individual cells" PNAS; vol. 98; No. 25; Nov. 27, 2001; pp. 14238-14243.
Zenklusen, Daniel and Singer, Robert H. "Analyzing mRNA Expression Using Single mRNA Resolution Fluorescent in Situ Hybridization" Methods in Enzymology, vol. 470, <https://www.ncbi.nlm.nih.gov/pmc/articles/PMC3162037/>, pp. 1-17, Mar. 1, 2010.
Zenklusen, Daniel and Singer, Robert H. "Analyzing mRNA Expression Using Single mRNA Resolution Fluorescent in Situ Hybridization" Methods in Enzymology, 2010, vol. 470, pp. 641-659.
Weibrecht, I. et al In situ detection of individual mRNA molecules and protein complexes or post-translational modifications using padlock probes combined with the in situ proximity ligation assay (2013) Nature Protocols 8(2): 355-372 (Year: 2013).

* cited by examiner

SEQUENCE LISTING

```
Sequence total quantity: 7
SEQ ID NO: 1            moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 1
tcttcagcgt tcccgaga                                                 18

SEQ ID NO: 2            moltype = DNA  length = 46
FEATURE                 Location/Qualifiers
misc_feature            1..46
                        note = Synthetic oligonucleotide
source                  1..46
                        mol_type = other DNA
                        organism = synthetic construct
modified_base           22
                        mod_base = OTHER
                        note = uracil
modified_base           27
                        mod_base = OTHER
                        note = uracil
SEQUENCE: 2
gtgtatcctg atcaaaaaag gtgcgctgac aaagcgcgcc tttttt                  46

SEQ ID NO: 3            moltype = DNA  length = 59
FEATURE                 Location/Qualifiers
misc_feature            1..59
                        note = Synthetic oligonucleotide
source                  1..59
                        mol_type = other DNA
                        organism = synthetic construct
modified_base           22
                        mod_base = OTHER
                        note = uracil
modified_base           27
                        mod_base = OTHER
                        note = uracil
SEQUENCE: 3
gtgtatcctg atcaaaaaag gtgcgctgac aaagcgcgcc tttttgatc aggatacac     59

SEQ ID NO: 4            moltype = DNA  length = 18
```

```
FEATURE              Location/Qualifiers
misc_feature         1..18
                     note = synthetic oligonucleotide
source               1..18
                     mol_type = other DNA
                     organism = synthetic construct
SEQUENCE: 4
tctcgggaac gctgaaga                                            18

SEQ ID NO: 5         moltype = DNA  length = 46
FEATURE              Location/Qualifiers
misc_feature         1..46
                     note = Synthetic oligonucleotide
source               1..46
                     mol_type = other DNA
                     organism = synthetic construct
modified_base        9
                     mod_base = OTHER
                     note = uracil
modified_base        14
                     mod_base = OTHER
                     note = uracil
SEQUENCE: 5
aaaaaaggtg cgctgacaaa gcgcgccttt tttgatcagg atacac              46

SEQ ID NO: 6         moltype = DNA  length = 13
FEATURE              Location/Qualifiers
misc_feature         1..13
                     note = Synthetic oligonucleotide
source               1..13
                     mol_type = other DNA
                     organism = synthetic construct
SEQUENCE: 6
gatcaggata cac                                                 13

SEQ ID NO: 7         moltype = DNA  length = 31
FEATURE              Location/Qualifiers
misc_feature         1..31
                     note = Synthetic oligonucleotide
source               1..31
                     mol_type = other DNA
                     organism = synthetic construct
SEQUENCE: 7
tctcgggaac gctgaagaga tcaggataca c                             31
```

METHODS FOR HIGH-THROUGHPUT LABELLING AND DETECTION OF BIOLOGICAL FEATURES IN SITU USING MICROSCOPY

RELATED APPLICATION DATA

This application is a continuation application which claims priority to U.S. patent application Ser. No. 16/200,831, filed on Nov. 27, 2018; which is a continuation application of U.S. patent application Ser. No. 15/325,577, filed on Jan. 11, 2017; which is a National Stage Application under 35 U.S.C. 371 of co-pending PCT application PCT/US15/39914 designating the United States and filed Jul. 10, 2015; which claims the benefit of U.S. Provisional Patent Application No. 62/023,226, filed on Jul. 11, 2014 each of which are hereby incorporated by reference in their entireties.

STATEMENT OF GOVERNMENT INTERESTS

This invention was made with government support under MH098977 and MH103910 awarded by National Institutes of Health (NIH) and under DE-FG02-02ER63445 awarded by U.S. Department of Energy (DOE). The government has certain rights in this invention.

SEQUENCE LISTING

The instant application contains a Sequence Listing which has been submitted electronically in XML format and is hereby incorporated by reference in its entirety. Said XML copy, created on Jan. 19, 2023, is named "Sequence_Listing_010498_01517_ST26" and is 12.9 KB in size.

FIELD

The present invention relates to methods and compositions for detecting, identifying, measuring, counting, and/or segmenting biological features in cells.

BACKGROUND

Current methods for detecting biological features in cells broadly fall into three categories: 1) affinity-based detection using synthetic or natural antibodies conjugated to a fluorescent moiety; 2) fusing biological features to recombinant fluorescent proteins; and 3) labelling biological features with dyes. These art-known methods enable quantitative detection and localization of target features in fixed and/or living cells in situ. However, methods known in the art at the time of filing suffer from the drawback of only being able to utilize a narrow range of spectral space for multiplexed detection. Further, methods known in the art at the time of filing are prone to artifacts due to e.g., autofluorescence and/or noise in the analog signal domain.

SUMMARY

Accordingly, novel compositions and methods for specifically labelling of biological features in living cells, followed by detection of associated barcodes in situ using fluorescent sequencing are provided.

Embodiments of the present invention are directed to methods that are broadly applicable to highly specific multiplex visualization and localization of biological features. Unlike technologies known by others in the art at the time of filing, such as e.g., the use of fluorescent proteins, antibodies, nucleic acid probes, and the like, the methods of the present invention provide a subset of possible sequences that can be used to identify individual features. By applying a sequence pattern identification and matching approach to object-based image analysis, the methods described herein enable very high multiplexing capacity, while effectively eliminating false positives due to autofluorescence and background noise. Biological features (e.g., proteins and nucleic acids, macromolecular complexes, subcellular structures, cells, cell projections, extracellular structures, cell populations, tissue regions, organs, and other biological structures of interest) can be easily identified without relying on low-throughput, manual annotation or traditional automated image processing methods having limited sensitivity and/or accuracy.

In certain exemplary embodiments, a method of labelling a subcellular component in vivo is provided. The method includes the steps of providing a cell expressing an RNA comprising a barcode, reverse transcribing the RNA to produce DNA, circularizing the DNA, and performing rolling circle amplification (RCA) to produce an amplicon. The method optionally includes the step of detecting the amplicon.

In certain aspects, the RNA comprises a localization sequence that targets the RNA to the subcellular component. In other aspects, the subcellular component is an organelle (e.g., one or any combination of a nucleus, a nucleolus, a mitochondria, a Golgi apparatus, an endoplasmic reticulum, a ribosome, a lysosome, a vacuole, an endocytic vesicle, an exocytic vesicle, a cytoskeleton and a chloroplast) or a subcellular region (e.g., of one or any combination of a plasma membrane, a cell wall and a ribosomal subunit). In still other aspects, expression of the RNA is controlled by a promoter selected from the group consisting of one or any combination of an inducible promoter, a cell type-specific promoter and a signal-specific promoter. In certain aspects, a promoter is an endogenous promoter. In other aspects, a promoter is an exogenous promoter.

In certain exemplary embodiments, a method of labelling a protein in vivo is provided. The method includes the steps of providing a cell that expresses an RNA comprising a barcode and that expresses a protein comprising an RNA binding domain, allowing the RNA and the protein to interact, reverse transcribing the RNA to produce DNA, circularizing the DNA, and performing RCA to produce an amplicon. The method optionally includes the step of detecting the amplicon.

In certain aspects, the protein further comprises a domain that localizes it to a subcellular component. The subcellular component can be an organelle (e.g., one or any combination of a nucleus, a nucleolus, a mitochondria, a Golgi apparatus, an endoplasmic reticulum, a ribosome, a lysosome, a vacuole, an endocytic vesicle, an exocytic vesicle, a cytoskeleton and a chloroplast) or a subcellular region (e.g., of one or any combination of a plasma membrane, a cell wall and a ribosomal subunit). In other aspects, expression of the RNA is controlled by a promoter selected from the group consisting of one or any combination of an inducible promoter, a cell type-specific promoter and a signal-specific promoter. In certain aspects, a promoter is an endogenous promoter. In certain aspects, a promoter is an exogenous promoter.

In certain exemplary embodiments, a method of determining a nucleic acid sequence in situ is provided. The method includes the steps of providing a cell expressing an RNA comprising a barcode, reverse transcribing the RNA to produce DNA, circularizing the DNA, performing RCA to produce an amplicon, and sequencing the amplicon. In certain aspects, the cell further expresses a protein comprising an RNA binding domain.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION OF CERTAIN EMBODIMENTS

Figure 1A:
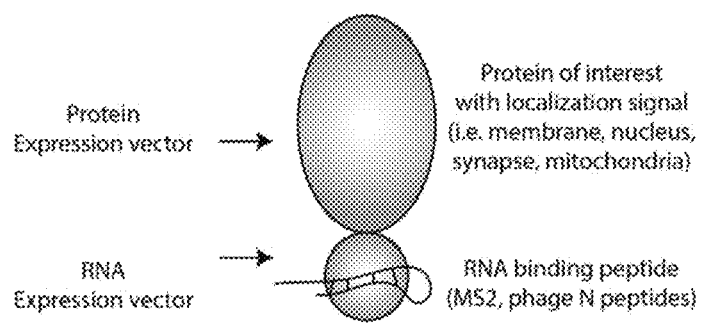
FIGS. 1A-1B schematically depict sequencing-compatible rolling circle amplification (RCA) amplicons cross-linked to a cell matrix and/or protein. (1A) A protein of interest is fused to a specific RNA binding protein (e.g., MS2, phage N peptides or the like) either at the N-terminus, the C-terminus or internally. A barcode-bearing RNA molecule with a stem-loop sequence that imparts high specificity binding is co-expressed in the cell. (1B) Cells are fixed and reverse transcription from internally primed stem loop RNA structures is used to convert RNA to DNA.

The present invention provides methods for detecting biological features in situ utilizing nucleic acid barcodes sequences. In certain exemplary embodiments, a cell expresses an exogenous nucleic acid sequence, e.g., an RNA sequence, that comprises a barcode. The barcode can serve as a label for the cell itself, and/or as a label for a subcellular component, e.g., an organelle or subcellular region of the cell. In certain aspects, the RNA sequence further comprises one or more localization sequences that direct RNA to one or more processing pathways (e.g., endogenous and/or exogenous) to localize the RNA sequence such that it can function as a barcode label for subcellular or extracellular features.

As used herein, the term "barcode" refers to a unique oligonucleotide sequence that allows a corresponding nucleic acid sequence (e.g., an oligonucleotide fragment) to be identified, retrieved and/or amplified. In certain embodiments, barcodes can each have a length within a range of from 4 to 36 nucleotides, or from 6 to 30 nucleotides, or from 8 to 20 nucleotides. In certain exemplary embodiments, a barcode has a length of 4 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

As used herein, the term "cellular component" refers to a portion of a prokaryotic or eukaryotic cell. A cellular component includes, for example, a cellular organelle, including, but not limited to, a nucleus, a nucleolus, a mitochondria, a Golgi apparatus, an endoplasmic reticulum, a ribosome, a lysosome, a vacuole, an endocytic vesicle, an exocytic vesicle, a vacuole, a cytoskeleton, a chloroplast, and the like. A cellular component can also include a subcellular region, including, but not limited to, a plasma membrane, cell wall, a ribosomal subunit, transcriptional machinery, cell projections, and the like.

In certain embodiments, cells expressing an exogenous RNA sequence also express one or more polypeptides comprising an RNA binding domain. RNA binding domains include four main families: RNA recognition motifs (RRMs), zinc fingers, KH domains and double-stranded RNA binding motifs (dsRBMs). (For a review, see Clery and Allain in Madam Curie Bioscience Database (2011), found at the ncbi[dot]nlm[dot]nih[dot]gov website.) Exemplary RNA binding domains include, but are not limited to, MS2, phage N peptides (such as, e.g., lambda phage or P22 phage N-peptides), and the like. A database of DNA binding domains suitable for use in the present invention can be found at the website rbpdb[dot]ccbr[dot]utoronto[dot]ca.

In certain aspects, the polypeptide is a nuclear, cytosolic or transmembrane protein or a portion thereof (e.g., a polypeptide), fused to one or more RNA binding domains, such that the RNA sequence can function as a barcode label for the fusion protein, allowing for highly parallel detection of proteins. The cellular origin of each RNA-barcode-bound fusion protein can be identified by sequencing the associated RNA barcode.

As used herein, the terms "peptide" and "polypeptide" include compounds that consist of two or more amino acids that are linked by means of a peptide bond. Peptides and polypeptides may have a molecular weight of less than 10,000 Daltons, less than 5,000 Daltons, or less than 2,500 Daltons. The terms "peptide" and "polypeptide" also include compounds containing both peptide and non-peptide components, such as pseudopeptide or peptidomimetic residues or other non-amino acid components. Such compounds containing both peptide and non-peptide components may also be referred to as a "peptide analogue" or a "polypeptide analogue."

As used herein, the term "protein" includes compounds that consist of amino acids arranged in a linear chain and joined together by peptide bonds between the carboxyl and amino groups of adjacent amino acid residues.

As used herein, the terms "attach" or "bind" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

In certain exemplary embodiments, biological features can be labelled as described herein using 4N unique RNA barcodes, wherein N is sequence length. Cellular components labelled as described herein can be identified by sequencing one or more associated RNA barcode labels. When a transmembrane protein is labelled, the membrane borders of 4N (wherein N is sequence length) cells can uniquely be identified using the RNA barcode for highly multiplexed membrane segmentation.

In certain exemplary embodiments, one or more components involved with intracellular or intercellular communication (e.g., involved with synapse formation, vesicle trafficking and the like) can be labelled by expressing a fusion protein encoding a localization domain specific to both the component and to an RNA binding domain in a cell. The expressed RNA barcode label can bind the fusion protein and be subsequently transported to a cellular component (e.g., organelle or subcellular region) of interest.

In accordance with certain examples, methods of sequencing barcodes in situ within an organism (e.g., in a cell or subcellular component (e.g., an organelle or a subcellular region)) are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra and U.S. Pat. Nos. 5,750,341 and 6,306,597, incorporated herein by reference.

FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes.

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes.

MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the barcodes within the organism or portion thereof can be interrogated in situ using methods known to those of skill in the art including fluorescently labelled oligonucleotide/DNA/RNA hybridization, primer extension with labelled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

According to one aspect, methods described herein produce a three dimensional nucleic acid amplicon within an organism or portion thereof which is stable, long-lasting and resistant, substantially resistant or partially resistant to enzymatic or chemical degradation. The three dimensional nucleic acid amplicon can be repeatedly interrogated using standard probe hybridization and/or fluorescence based sequencing. The three dimensional nucleic acid amplicon can be repeatedly interrogated with little or no signal degradation, such as after more than 50 cycles, and with little position shift, such as less than 1 µm per amplicon.

In certain aspects, the fusion protein substitutes for traditional reporter proteins, such as fluorescent reporter proteins (e.g., green fluorescent protein (GFP), mCherry, and the like) in fixed cells to perform multiplexed protein localization studies, in which barcode sequences, rather than a specific fluorescent signal, define the label. In certain aspects, the fusion protein can substitute or complement immunocytochemistry, in which barcode sequences, rather than a limited range of colors from secondary antibodies, are used to define the label.

In certain exemplary embodiments, digital images are generated by fluorescent sequencing of barcode labels that are combined to create a composite image, in which all channels and images over time are spatially registered. The composite image would then contain potential signals at each pixel, with real signals corresponding to nucleic acid sequences, which are distinguishable from objects not of interest (e.g. dirt, autofluorescence, and the like) by the nature and/or content of the sequence signals.

The nature of expected sequence patterns and the space of potential sequence patterns encompassing the barcode labels serve as a priori information in object-based image analysis algorithms to identify objects and measure object attributes. Object identification does not rely on algorithms utilizing intensity-based thresholds, high signal-to-noise ratio, or other object features such as shape. Thus, it is much more sensitive for quantitative detection of molecular analytes or cellular features.

The variable region of an RNA comprising a barcode sequence may be generated randomly or may be designed. Variable regions can be constructed using nucleic acid synthesis methods or in vivo by recombination. An RNA comprising a barcode sequence can contain 'error-correcting' sequences to compensate for a possible sequencing error. An RNA comprising a barcode sequence may contain on or more RNA localization signals to the direct the cell to localize the RNA barcode molecules to specific subcellular and/or extracellular regions. An RNA comprising a barcode sequence can be polyadenylated to promote efficient nuclear export.

In certain exemplary embodiments, RNA-binding proteins as described further herein (e.g., MS2, lambda N peptide, P22 N peptide, and the like) or a portion thereof are fused in frame to a protein of interest at the N-terminus or the C-terminus end. These peptides are capable of binding their cognate sequence (e.g., a conserved RNA hairpin stem sequences) with high affinity. A protein of interest can be cytosolic, nuclear, or membrane-spanning, bearing a protein localization signal (i.e. cadherin, synapsin, histone, transcription factors). A protein of interest can be expressed by integrating or epi-chromosomal expression vectors delivered, e.g., by transfection or viral infection.

An RNA comprising a barcode sequence may be converted into cDNA by endogenous or exogenous biochemical means. The 3' end of an RNA comprising a barcode sequence can contain an RNA stem loop structure enabling efficient self-primed cDNA synthesis when cells are fixed and treated with a reverse transcription reaction mixture. The RNA:DNA hybrid formed after reverse transcription can be enzymatically processed using a combination nucleases and/or restriction enzymes, leaving single stranded cDNA of a fixed length, which can then be circularized and amplified by rolling circle amplification. The 3' an RNA comprising a barcode sequence end of the transcript can contain a RNA stem loop structure necessary for binding to e.g., MS2, phage N peptides, or any other sequence specific peptide domains.

In certain exemplary embodiments, an RNA:DNA complex is degraded and/or processed to yield a 5' phosphorylated single-stranded DNA molecule, allowing the cDNA barcode to be circularized, such as by enzymes like special DNA ligase sold under the trademark CircLigase™. Rolling circle amplification can then be used to generate multiple tandem copies of the barcode in situ. Aminoallyl dUTP and crosslinkers can be to immobilize the amplicons, e.g., within an organism (e.g., in a cell or cellular component (e.g., an organelle or a subcellular region)). A primer complementary to the constant region of the barcode may be used to prime rolling circle amplification.

Certain aspects of the invention pertain to vectors, such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein (e.g., a nucleic acid sequence encoding an RNA having a barcode sequence and/or a nucleic acid sequence encoding a polypeptide (e.g., a fusion protein)) is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy ori can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, WI). For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. In certain aspects, operably linked nucleic acid sequences are physically linked, using e.g., fusion RNAs and/or fusion proteins without splicing and/or cleavage of the endogenous product and recombinant nucleic acid sequences. The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a virosome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, CA), LIPOFECTAMINE® (Invitrogen), FUGENE® (Roche Applied Science, Basel, Switzerland), JETPEI™ (Polyplus-transfection Inc., New York, NY), EFFECTENE® (Qiagen, Valencia, CA), DREAMFECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, IPL, IPR, T7, tac, and trc (useful for expression in Escherichia coli and Pseudomonas); the amy, apr, npr promoters and various phage promoters useful for expression in Bacillus subtilis, and Bacillus licheniformis; nisA (useful for expression in gram positive bacteria, Eichenbaum et al. Appl. Environ. Microbiol. 64(8):2763-2769 (1998)); and the synthetic P11 promoter (useful for expression in Lactobacillus plantarum, Rud et al., Microbiology 152:1011-1019 (2006)). Termination control regions may also be derived from various genes native to the preferred hosts.

In certain exemplary embodiments, an RNA comprising a barcode sequence can be expressed through transcription. Endogenous or exogenous promoters, such as U6 or H1, can drive expression of the RNA comprising a barcode sequence. The RNA comprising a barcode sequence may contain a common region for primer-based amplification and/or sequencing. The term RNA barcode may refer to a variable region alone or to both a variable and a common region, since in some instances the common region is used to provide a read-out of the variable region.

In certain exemplary embodiments, an RNA comprising a barcode sequence can be encoded by a genomic locus. In other exemplary embodiments, an RNA comprising a barcode sequence can be encoded by a vector. In certain aspects, an expression module is present in a fusion protein expression vector. In other exemplary embodiments, an RNA comprising a barcode sequence is delivered directly to a cell by transfection, in which a single RNA barcode oligonucleotide or a library of RNA barcode oligonucleotides is added exogenously.

Expression of an RNA comprising a barcode sequence can be signal-dependent and/or context-specific. For example, cell type-specific or signal-specific promoters can be used to express an RNA comprising a barcode sequence in a desired population of the cells so that only cellular components and/or proteins in responsive cells are labelled with the RNA comprising a barcode sequence. Expression of an RNA comprising a barcode sequence can be inducible (e.g., with doxycycline) in order to avoid toxic effects of prolonged single stranded RNA overexpression.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in gram negative bacteria (Scott et al., Plasmid 50(1):74-79 (2003)). Several plasmid derivatives of broad-host-range Inc P4 plasmid RSF1010 are also available with promoters that can function in a range of gram negative bacteria. Plasmid pAYC36 and pAYC37, have active promoters along with multiple cloning sites to allow for the heterologous gene expression in gram negative bacteria.

Chromosomal gene replacement tools are also widely available. For example, a thermosensitive variant of the broad-host-range replicon pWV101 has been modified to construct a plasmid pVE6002 which can be used to create gene replacement in a range of gram positive bacteria (Maguin et al., J. Bacteriol. 174(17):5633-5638 (1992)). Additionally, in vitro transposomes are available to create random mutations in a variety of genomes from commercial sources such as EPICENTRE® (Madison, WI).

Vectors useful for the transformation of E. coli are common and commercially available. For example, the desired genes may be isolated from various sources, cloned onto a modified pUC19 vector and transformed into E. coli host cells. Alternatively, the genes encoding a desired biosynthetic pathway may be divided into multiple operons, cloned into expression vectors, and transformed into various E. coli strains.

Features or objects may be of a biological nature, such as molecules, subcellular compartments, projections, cells, groups of cells, regions of tissue, tissues, or organs. Biological features may be made to have the characteristics described above by sequencing synthetic or natural, endogenous or exogenous, nucleic acid molecules spatially organized by any method, familiar to those with skill in the art.

Analysis of objects using methods described herein may be combined with or compared to other images of the sample that have been stained with membrane- and organelle-specific dyes, antibodies, or reporter proteins.

In certain embodiments, nucleic acids are those found naturally in a biological sample, such as a cell or tissue.

Embodiments of the present invention are directed to methods of amplifying nucleic acids in situ within an organism or portion thereof (e.g., cell (e.g., cellular component, e.g., organelle and/or subcellular region), tissue, organ or the like) by contacting the barcode with reagents and under suitable reaction conditions sufficient to amplify the barcode. According to one aspect, the organism or portion thereof is rendered porous or permeable to allow migration of reagents into the matrix to contact the barcode. In certain aspects, barcodes are amplified by selectively hybridizing an amplification primer to an amplification site at the 3' end of the barcode using conventional methods. Amplification primers are 6 to 100, and even up to 1,000, nucleotides in length, but typically from 10 to 40 nucleotides, although oligonucleotides of different length are of use.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanehisa, M., 1984, Nucleic Acids Res. 12: 203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30: e43, and Rouillard et al. (2004) Nucleic Acids Res. 32: W176, incorporated by reference herein in their entirety for all purposes).

In accordance with an additional aspect, kits are provided. In one aspect, the kits comprise a cell described herein, and optionally, instructions for use.

According to one aspect, nucleic acids are modified to incorporate a functional moiety for attachment to a matrix. The functional moiety can be covalently crosslinked, copolymerize with or otherwise non-covalently bound to the matrix. The functional moiety can react with a crosslinker. The functional moiety can be part of a ligand-ligand binding pair. DNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is crosslinked to modified dNTP or dUTP or both. Suitable exemplary crosslinker reactive groups include imidoester (DMP), succinimide ester (NETS), maleimide (Sulfo-SMCC), carbodiimide (DCC, EDC) and phenyl azide. Crosslinkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, crosslinked agarose, crosslinked dextran or crosslinked polyethylene glycol. The matrix forming materials can form a matrix by polymerization and/or crosslinking of the matrix forming materials using methods specific for the matrix forming materials and methods, reagents and conditions known to those of skill in the art. In certain aspects, the structure of a matrix is static, e.g., the matrix has a stable three-dimensional state. In other aspects, the matrix is flexible, e.g., one or more of matrix size, shape, etc. can be altered or modified such that higher spatial resolution is achieved and/or additional downstream analyses cab be performed, e.g., mass spectroscopy and the like.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional crosslinkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional crosslinkers are then added to allow the formation of a gel matrix. The un-incorporated material is washed out and any remaining functionally reactive group is quenched. Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids are immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise crosslinking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the crosslinking density. Additional control over the molecular sieve size and density is achieved by adding additional crosslinkers such as functionalized polyethylene glycols. According to one aspect, the nucleic acids, which may represent individual bits of information, are readily accessed by oligonucleotides, such as labelled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include a next-generation DNA sequencing technology sold under the trademark SoLiD™ Supported Oligonucleotide Ligation and Detection) (ABI Life Technologies), in which a sequencing primer on a template is ligated to a library of fluorescently labelled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The overflow is achieved using an automated fluidics and imaging device (i.e. a next-generation DNA sequencing technology sold under the trademark SoLiD™ (Supported Oligonucleotide Ligation and Detection) 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (a high-throughput sequencing system sold under the trademark HiSeq™, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

According to one aspect, a plurality of circular DNA molecules are covalently linked to one another. The circular DNA molecules are then amplified using methods known to those of skill in the art, such as isothermal enzymatic amplification one example of which is RCA. According to this aspect, the amplicons are localized near the circular DNA. According to this aspect, the amplicons form a shell around the circular DNA or otherwise assemble around the circular DNA. Each circular DNA may have more than 1000 amplicons surrounding or otherwise associated therewith. According to this aspect, the amplicons surrounding a particular circular DNA provide a high signal intensity, due in part to the number of amplicons and/or detectable labels associated with the amplicons.

The amplicons may be functionalized and crosslinked or otherwise covalently bound together around their associate circular DNA to form a series or network of tightly bound DNA amplicon shells around each circular DNA. The series or network of tightly bound DNA amplicon shells around each circular DNA may be assembled onto a three-dimensional support. According to one aspect, the series or network of tightly bound DNA amplicon shells around each circular DNA may be assembled onto a three-dimensional support producing a three dimensional DNA polymer with defined overall shape, size and amplicon position.

According to one aspect, amplicons are covalently linked without the need for separate crosslinkers, such as bis-N-succinimidyl-(nonaethylene glycol) ester. An acrydite moiety, such as a catalyst activated acrydite moiety is introduced at the end of a long carbon spacer (i.e., about C6 to about C12) at position 5 of a uracil base a representative formula of which is shown below.

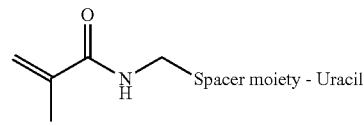

In the formula below, R represents the acrydite spacer moiety attached to the 5 position of the uracil base.

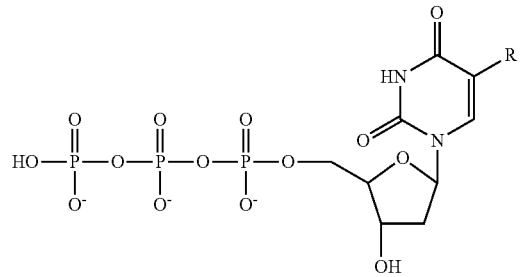

When copolymerized with bis-acrylamide in the presence of a catalyst, a polymerization reaction takes place, encapsulating the circular DNA with the amplicons and fixing the amplicons in position. The chemically inert nature of the polymerized mixture allows various downstream applications. The spacer can be a carbon chain of between about 2 carbons to about 200 carbons. The spacer can be polyethylene glycol. The length of the spacer can vary from about 30 angstroms to about 100 angstroms and can be of various molecular weights. The spacer can be permanent or reversible, such as by using UV light, enzymes, chemical cleavage, etc.

A three dimensional matrix, such as a polyacrylamide gel matrix, can be used to embed a variety of biological structures containing enzymatically or chemically modified DNA or RNA molecules containing an acrydite functional moiety. The non-nucleic acid component is selectively dissolved using detergents, proteases, organic solvents or denaturants to create a three dimensional matrix that preserves individual DNA or RNA molecules and their relative spatial location. Examples include embedding cells, healthy and diseased tissues and tissue sections, small model organisms such as worms and insects, bacterial colonies or biofilms, environmental samples containing other DNA or RNA containing materials or organisms.

In certain exemplary embodiments, an object-based image analysis (OBIA) algorithm is used to analyze barcode sequences. The OBIA algorithm applies pattern identification and matching sequences to partition images into objects and measure object properties, given the objects are properly labelled with sufficiently long DNA or RNA barcode sequences. The actual sequence profile of an object is a subset of the total potential sequence space. Objects are identified through a priori information about the expected sequence patterns and the space of potential sequence patterns.

As used herein, a "digital image data" refers to a numeric representation of values corresponding to measured signals distributed in two- or three-dimensional space over time. The map may be stored using raster or vector format. The signals measured are generated using sequencing methods described above. Sequencing signals are characterized as a temporal pattern within the digital image data, such that the total signal profile is a subset of the total possible signal space. Digital image data can be processed using methods such as deconvolution, registration, normalization, projection, and/or any other appropriate mathematical transformations known in the art. Images are registered over time.

As used herein, the term "pattern identification OBIA" refers to the identification and characterization of an object within the image data by identifying the temporal pattern using prior information about the nature of expected patterns. According to this aspect of the invention, pixels are identified as objects or spatially clustered into objects by identifying pixels with the characteristics listed above. According to one aspect of the invention, objects are identified using the expectation that they consist of one or more spatially correlated pixels with a particular temporal sequence of signals.

As used herein, the term "pattern matching OBIA" refers to the identification and characterization of an object within the image data by matching the sequence patterns of individual pixels or composite patterns of groups of pixels to a reference set of expected patterns. In certain aspects of the invention, the patterns compared to the reference may be a subset of all patterns present in the image. In other aspects of the invention, all patterns in the data may be compared to the reference. According to certain aspects of the invention, patterns in the data may be compared and matched to the expected reference patterns by search methods and/or computation of distance metrics or probability functions familiar to those with skill in the art.

A reference characteristic may consist of nucleic acid sequences, including genomic or transcriptomic sequences as well as synthetic, artificial, or programmed sequences of nucleic acids. The reference characteristic may consist of any previously known set of patterns with the characteristics listed above.

Computational tasks related to OBIA are executed using the pattern identification and/or pattern matching methods, including feature recognition, segmentation, object tracking, object counting, object disambiguation, object reconstruction, and spatial classification. Sequence pattern identification and matching described above may be used for computational image processing tasks, such as image stitching, registration, filtering, colorization, parameterization, and noise reduction. For instance, objects in the digital image data with patterns not matched in the reference may be excluded from visualization and subsequent analysis. Remaining pixels may be false colored, filtered, or otherwise represented as a high-dynamic range image; with dynamic range sufficient to represent the space of identified sequences. This reduces the impact of autofluorescence and background noise from cellular debris in visualization and downstream analysis. Image registration and stitching algorithms can be designed to maximize the number of objects identified using methods described above.

Certain exemplary embodiments are directed to the use of computer software to automate design and/or interpretation of genomic sequences, mutations, oligonucleotide sequences and the like. Such software may be used in conjunction with individuals performing interpretation by hand or in a semi-automated fashion or combined with an automated system. In at least some embodiments, the design and/or interpretation software is implemented in a program written in the JAVA programming language. The program may be compiled into an executable that may then be run from a command prompt in the WINDOWS XP operating system. Unless specifically set forth in the claims, the invention is not limited to implementation using a specific programming language, operating system environment or hardware platform.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables and accompanying claims.

Example I

RCA Amplicon Analysis

Figure 1B:
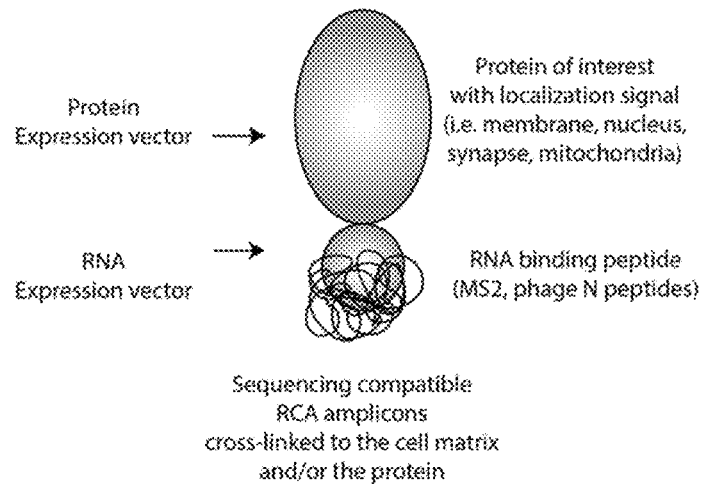
Figure 2:
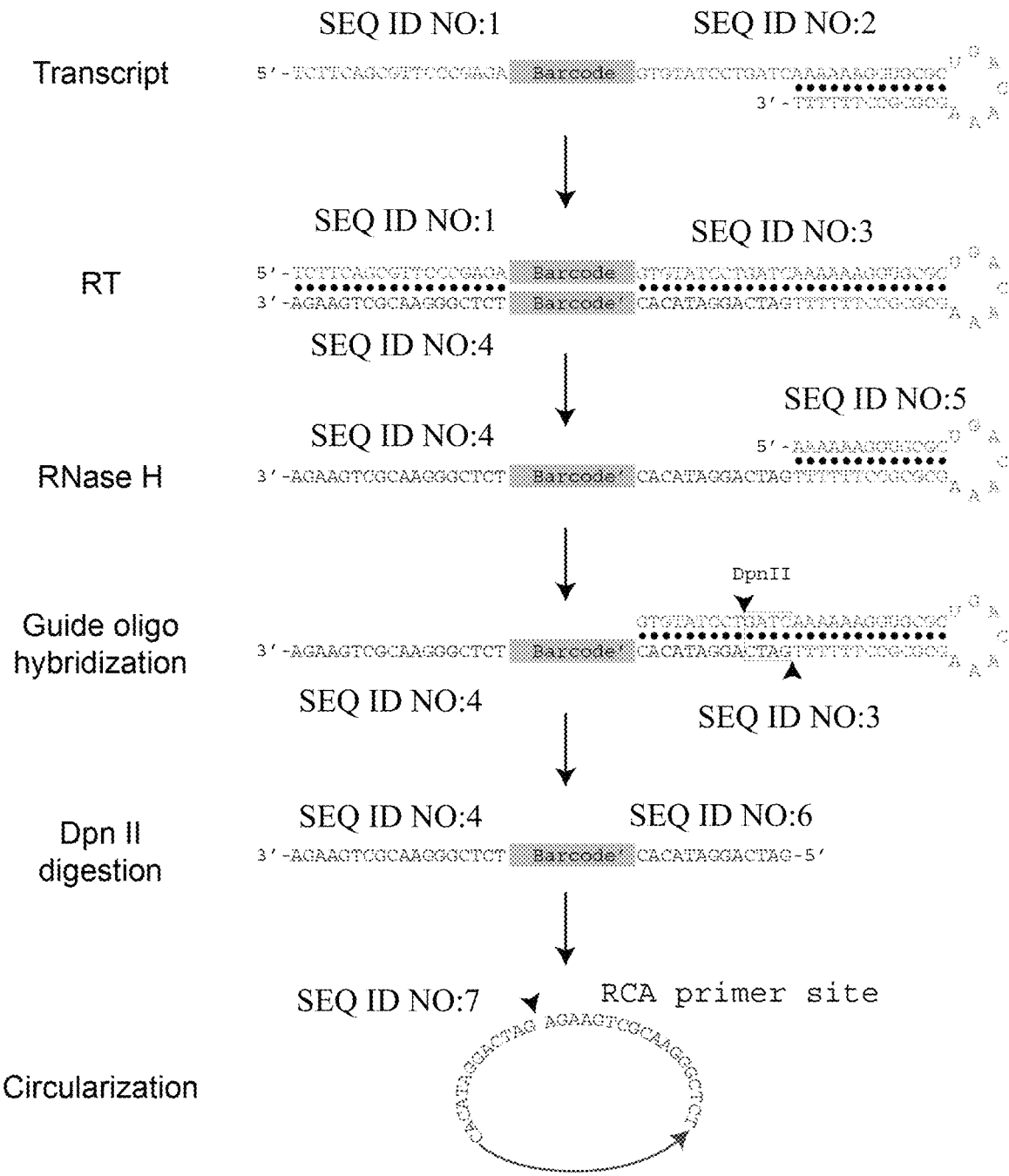
FIG. 2 schematically depicts a method for efficiently generating DNA amplicons from bar code-bearing RNA molecules according to certain aspects of the invention. Synthesis of DNA from complementary RNA in situ is improved by using the end of the stem-loop structure, which also serves as the recognition site for the RNA binding protein. After reverse transcription (RT), RNases are used to remove much of the RNA, while an additional cleavage step is performed using a guide oligo and a restriction enzyme that processes the 5' end of the DNA for efficient circularization. RCA is then used to generate tandem copies of the DNA, enabling molecular sequencing in situ with a high signal-to-noise ratio. The figure discloses transcript sequences as SEQ ID NOS 1 and 2; RT sequences as SEQ ID NOS 1, 3, and 4; RNase H sequences as SEQ ID NOS 5 and 4; Guide oligo hybridization sequences as SEQ ID NOS 3 and 4; Dpn II digestion sequences as SEQ ID NOS 6 and 4; and circularization sequence as SEQ ID NO: 7, all respectively, in order of appearance, identified in the 5' to 3' orientation.
Figure 3:
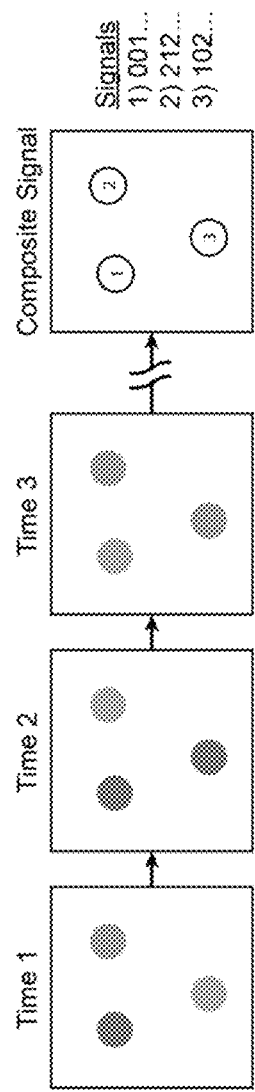
FIG. 3 schematically depicts digital images generated by fluorescent sequencing of barcode labels that are combined to create a composite image in which all channels and images over time are spatially registered. The composite image contains potential signals at each pixel. Real signals corresponding to nucleic acid sequences are distinguishable from objects not of interest (e.g., dirt, autofluorescence and the like) by the nature and/or content of the sequence signals. The nature of sequencing reactions can be programmed to give k signals per time point over N time points. Biological features can be labelled with kN unique barcodes.
Figure 4:
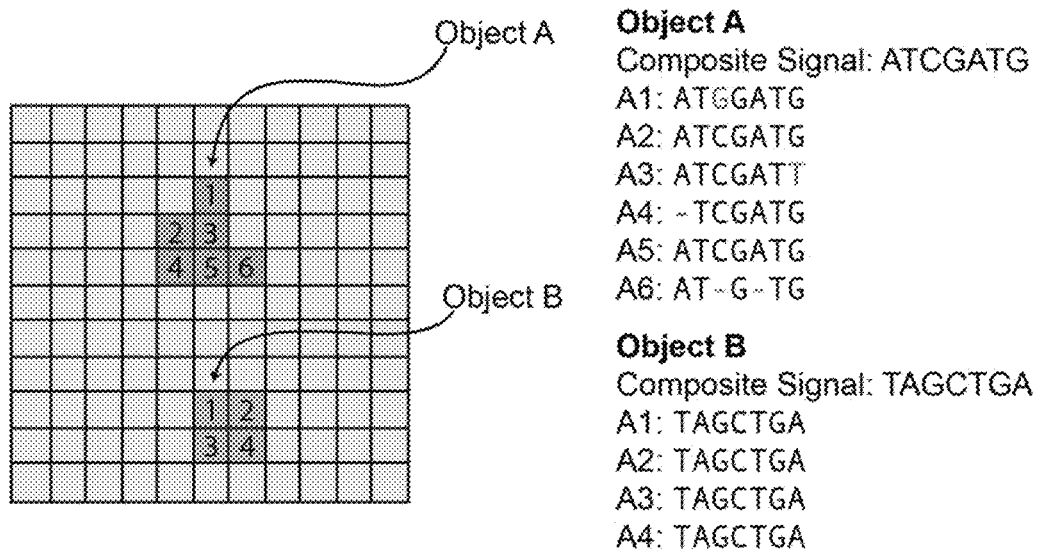
FIG. 4 schematically depicts the identification of two objects among the pixels of the image by the nature of their sequence patterns, i.e., they have signal at each sequencing base in only one channel, sustained over all sequencing reactions. The pixels constituting object A do not match each other perfectly, but a custom distance function clusters these as sufficiently similar to belong to the same object, and a composite sequence is generated. The pixels constituting object B each share identical sequences.
Figure 5:
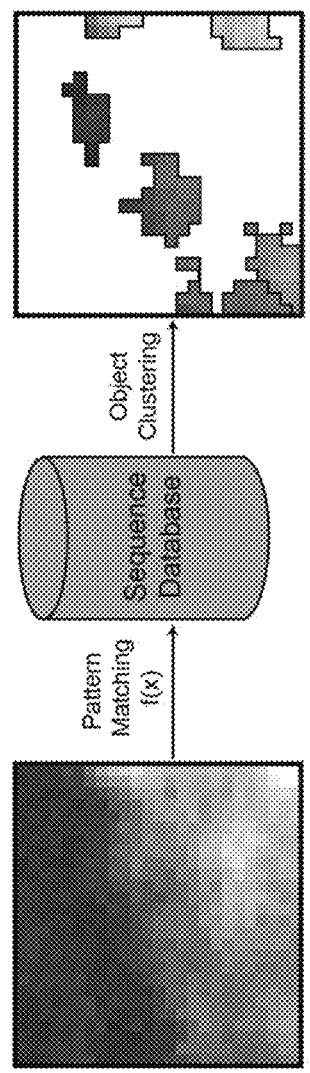
FIG. 5 schematically depicts the identification of objects by matching the sequence patterns in all pixels to a reference sequence database. Connected components (pixels) with shared sequences (or with shared matches to sequence patterns) are clustered to identify objects. Pixels without sequences in the reference sequence database are filtered out of the final image (e.g., background, noise, dirt, autofluorescence and the like). The attributes of each object, such as size, shape and genetic content, can be computed and used in downstream analyses.

A protein of interest is fused to a specific RNA binding protein and a barcode bearing RNA molecule is co-expressed in the cell (FIG. 1A). Cells are then fixed, and reverse transcribed from internally primed stem loop RNA structures are used to convert RNA to DNA (FIG. 1B). In certain aspects, the DNA is circularized using a special DNA ligase sold under the trademark CircLigase™ and amplified using Phi29 DNA polymerase. Crosslinker compatible nucleotides are incorporated during reverse transcription and rolling circle amplification. Crosslinkers can then be used to attach nucleotides to a subcellular component (e.g., the cell matrix and/or one or more proteins and/or attached to a synthetic three-dimensional support matrix (e.g., copolymerized in an acrylamide gel). The single molecule amplicons are sequenced using direct DNA ligation, extension, or hybridization using fluorescently labelled probes. The sequential images from multiple sequencing or hybridization cycles are used to generate sequencing reads from each protein-RNA complex. The barcode sequence is then used to identify individual proteins and where the RNA is transcribed.

Example II

Cell Segmentation

Cells expressing an RNA barcode widely throughout the cell body are labelled and segmented by using the barcode sequence to identify the space occupied by each cell.

Example III

Multiplex Membrane Labelling

Using a fusion protein encoding membrane-specific proteins and cells that bear a single copy of the RNA barcode via site-specific recombination, a large number of cells are labelled with unique RNA barcodes localized to the cell membrane inner surface. This information, coupled with the use of complementary membrane dyes or proteins, enables a large number of cellular membranes to be uniquely identified and segmented. This allows one of ordinary skill in the art the ability to accurately assess single cell biology using, e.g., cell culture, tissue sections, and/or developing embryos.

Example IV

Brain Synapse Mapping

Figure 6:
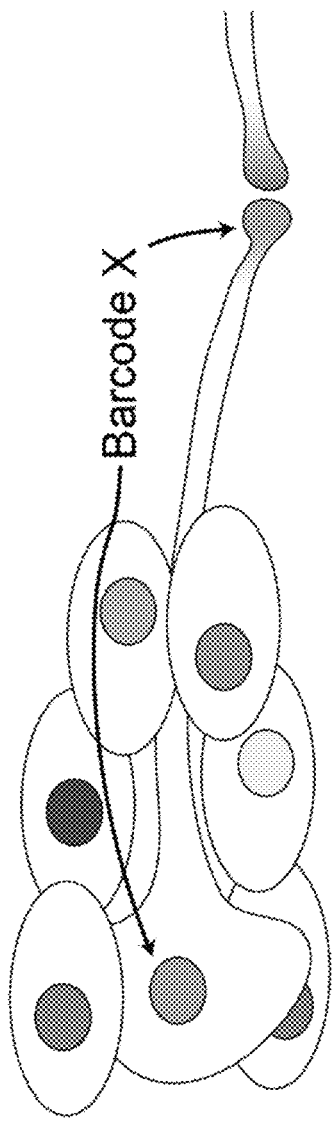
FIG. 6 schematically depicts neurons that are reconstructed using the methods described herein in which RNA barcodes are expressed in the nuclei or cell bodies, as well as in the synapse. Distant synapses are uniquely linked to the projecting cell body through the RNA barcode. The nuclear barcode is expressed but not polyadenylated, and is therefore localized to the nucleus without coupling to RNA-binding protein. The synapse is labelled with RNA barcode coupled to RNA-binding protein domain fused to a synapse-localizing proteins such as, e.g., neurexin.

By fusing the RNA binding domain to one or more pre-synaptic or post-synaptic proteins (e.g., neurexin, neuroligin, synapsin, NMDA receptor and the like) along with a cell-specific RNA barcode, the physical location of individual synapses and their cellular origins are imaged in a high-throughput manner. (See FIG. 6.) Each barcode also contains information regarding the identity of fusion proteins, such that a proper pairing of pre-synaptic and post-synaptic proteins can be identified using a co-localization matrix. In certain aspects, expression of the fusion protein and/or RNA barcode is activity-dependent, such that only those neurons and their synapses that are functionally active are imaged selectively. Synapses are then uniquely associated with the cells that generate them.

Example V

Monitoring Intra-Cellular and/or Inter-Cellular Trafficking

RNA binding domains are specifically fused to vesicle-specific and/or exosome-specific proteins to track multiple vesicles and/or exosomes to their originating cells.

What is claimed is:

1. A method for processing a nucleic acid molecule in a cell, comprising:
   (a) reverse transcribing an RNA molecule comprising a stem-loop structure in a cell, wherein said RNA molecule self-primes complementary DNA (cDNA) synthesis, thereby producing a first intermediate nucleic acid molecule comprising RNA, DNA, and said stem-loop structure;
   (b) removing said stem-loop structure from said first intermediate nucleic acid molecule or derivative thereof to produce a single-stranded DNA molecule; and
   (c) amplifying said single-stranded DNA molecule or derivative thereof to generate a DNA amplicon in said cell.

2. The method of claim 1, wherein (b) comprises using a restriction enzyme to remove said stem-loop structure from said first intermediate nucleic acid molecule or derivative thereof.

3. The method of claim 2, wherein (b) further comprises:
   (i) using an RNase to remove an RNA segment from said first intermediate nucleic acid molecule, thereby producing a second intermediate nucleic acid molecule, and
   (ii) using said restriction enzyme to remove said stem-loop structure from said second intermediate nucleic acid molecule, thereby producing said single-stranded DNA molecule.

4. The method of claim 3 further comprising, prior to (ii), hybridizing a guide oligonucleotide to said second intermediate nucleic acid molecule and contacting said guide oligonucleotide with said restriction enzyme.

5. The method of claim 1, further comprising, prior to (c), circularizing said single-stranded DNA molecule to generate a circularized nucleic acid molecule.

6. The method of claim 5, wherein (c) comprises conducting a rolling circle amplification reaction using said circularized nucleic acid molecule as a template.

7. The method of claim 1, wherein said RNA molecule comprises a barcode sequence.

8. The method of claim 7, wherein said DNA amplicon comprises said barcode sequence.

9. The method of claim 8, further comprising detecting said barcode sequence.

10. The method of claim 1, wherein said DNA amplicon comprises a crosslinker compatible nucleotide capable of cross-linking with a surface of a subcellular component of said cell.

11. The method of claim 10, wherein said crosslinker compatible nucleotide comprises an amine, acrydite, alkyne, biotin, azide, or thiol.

12. The method of claim 10, wherein (c) comprises amplifying said single-stranded DNA molecule or derivative thereof in a presence of said crosslinker compatible nucleotide, to generate said DNA amplicon comprising said crosslinker compatible nucleotide.

13. The method of claim 10, further comprising crosslinking said DNA amplicon comprising said crosslinker compatible nucleotide to said subcellular component.

14. The method of claim 1, wherein said RNA molecule is a messenger RNA (mRNA).

* * * * *